(12) United States Patent
Viachaslau et al.

(10) Patent No.: US 8,876,977 B2
(45) Date of Patent: Nov. 4, 2014

(54) METHOD FOR CLEANING THE U-TUBE OF THE MEASUREMENT CELL OF A DENSIMETER

(75) Inventors: Urvantsau Viachaslau, Fontenay le Marmion (FR); Marie Patrick, Rots (FR)

(73) Assignee: Instrumentation Scientifique de Laboratoire, Verson (FR)

( * ) Notice: Subject to any disclaimer, the term of this patent is extended or adjusted under 35 U.S.C. 154(b) by 416 days.

(21) Appl. No.: 13/173,185

(22) Filed: Jun. 30, 2011

(65) Prior Publication Data

US 2012/0073598 A1  Mar. 29, 2012

(30) Foreign Application Priority Data

Jul. 2, 2010  (FR) ..................................... 10 55357

(51) Int. Cl.
*B08B 7/02* (2006.01)
*B08B 9/027* (2006.01)
*B08B 3/12* (2006.01)
*A61L 2/025* (2006.01)
*B08B 9/032* (2006.01)
*G01N 9/00* (2006.01)

(52) U.S. Cl.
CPC . *B08B 3/12* (2013.01); *B08B 9/032* (2013.01); *B08B 2209/005* (2013.01); *G01N 9/00* (2013.01)

USPC .............................. 134/1; 134/22.12; 134/34

(58) Field of Classification Search
CPC ..................... A61L 2/025; G01N 2291/02818; B08B 3/04; B08B 3/12; B08B 9/027; B08B 2209/005
USPC ............... 134/1, 22.11, 23, 22.12, 34; 422/20
See application file for complete search history.

(56) References Cited

U.S. PATENT DOCUMENTS 3,728,893 A * 4/1973 Janssen .......................... 73/32 A
4,690,560 A * 9/1987 Coogan .......................... 356/338

* cited by examiner

*Primary Examiner* — Michael Kornakov
*Assistant Examiner* — Natasha Campbell
(74) *Attorney, Agent, or Firm* — Faegre Baker Daniels LLP

(57) ABSTRACT

A method for cleaning the U-tube of the measurement cell of a densimeter, the measurement cell including an isothermic enclosure defining a measurement chamber closed by a stopper surrounded by a resilient seal, a U-tube extending inside the measurement chamber for containing a sample, the U-tube secured to the stopper at a base of the U-tube which includes free ends projecting outwardly from the measurement chamber to permit injection of the sample via an injection opening and evacuation of the sample via an evacuation opening, and means for causing the U-tube to vibrate. The method comprises, following a step of analyzing a sample, injecting a rinsing solvent into the injection opening of the U-tube, and subjecting the stopper to ultrasonic waves.

4 Claims, 1 Drawing Sheet

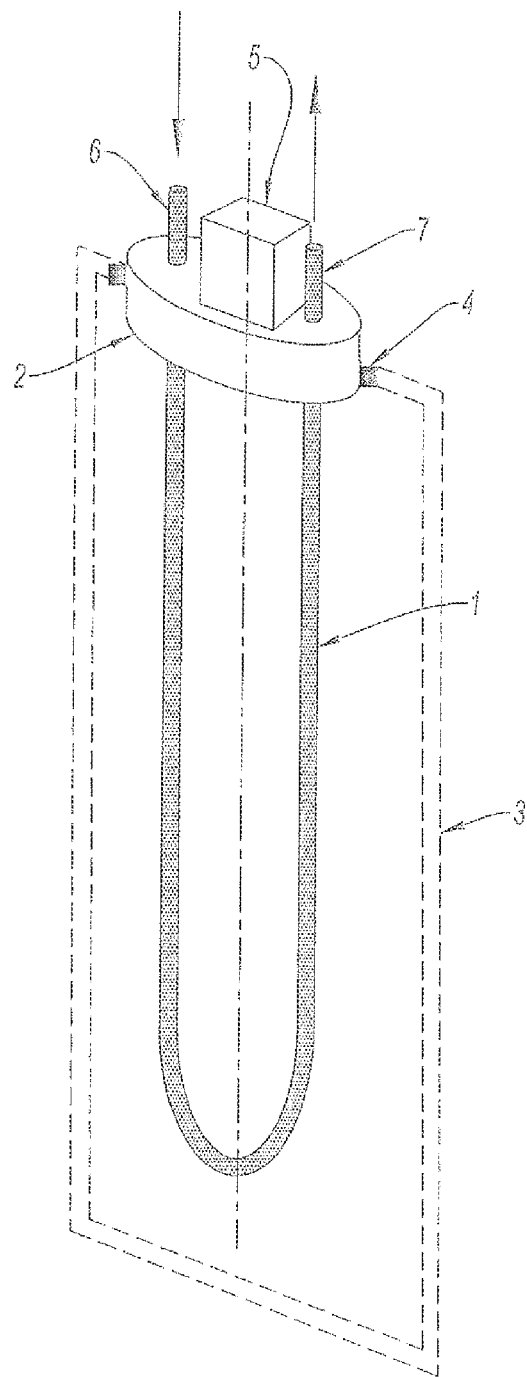

METHOD FOR CLEANING THE U-TUBE OF THE MEASUREMENT CELL OF A DENSIMETER

CROSS-REFERENCE TO RELATED APPLICATION

This application claims priority to French Patent Application No. 10 55 357 filed Jul. 2, 2010, the disclosure of which is hereby explicitly incorporated by reference herein.

BACKGROUND OF THE INVENTION

1. Field of the Invention

The present invention relates to a method for cleaning the U-tube of the measurement cell of a densimeter.

2. Description of the Related Art

Of the physical measurements which have to be effected in the context of industrial processes, that of density figures among the most frequently necessary.

To that end, manufacturers market a range of densimeters based on various principles, all of which have advantages and disadvantages.

A densimeter which can be used in a satisfactory manner to measure the density of a sample is equipped with a measurement cell comprising the following elements:

- an isothermic enclosure which defines at its inner portion a measurement chamber closed by a stopper surrounded by a resilient seal;
- a U-tube which is to be filled with a sample being analyzed and which extends inside the measurement chamber, the U-tube being secured to the stopper at its base, which is formed by its free ends which project outwardly from the measurement chamber in order to permit the injection of the sample being analyzed via an injection opening and its evacuation via an evacuation opening; and
- means for causing the U-tube to vibrate, as well as means for measuring the vibratory response of that tube.

By way of example, the U-tube can be kept earthed and the means for causing the tube to vibrate may be formed by:

- a ferromagnetic member with which the U-tube is equipped at its middle portion;
- an insulated conductive reading plate maintained at a difference in potential relative to the U-tube and secured to the stopper in a position facing that tube in order to define a capacitor therewith; and
- an electromagnetic excitation winding mounted at right-angles to the ferromagnetic member.

The principle of measuring the density of a sample by means of such a densimeter consists in causing the U-tube to vibrate at resonance frequency and in determining that frequency from the variations in the voltage at the terminals of the capacitor.

The resonance frequency enables the density of the sample being analyzed to be calculated to a first approximation on the basis of a standard equation known per se and from a preliminary calibration of the densimeter.

After each analysis, it is necessary to clean and rinse the U-tube of the measurement cell very carefully in order not to impair the subsequent analysis owing to the presence of sample residues deposited on the walls of the tube.

Such cleaning is a particularly long and inconvenient operation in as much as it requires the implementation of several successive steps.

The first of those steps consists in injecting via the injection opening of the U-tube, under pressure or by suction, a first solvent or rinsing solvent which must necessarily be compatible with the sample previously analyzed and evacuated via the evacuation opening, that is to say, it must be capable of dissolving that sample.

The rinsing solvent can be injected in the form of a homogeneous flux or in the form of a foam.

After the evacuation of the first solvent via the evacuation opening, it is necessary to inject via the injection opening a second, volatile, solvent or drying solvent which must then likewise be evacuated via the evacuation opening before the tube is dried by ventilation.

Such a method has a large number of disadvantages, the first of which is associated with the necessity to use significant amounts of two different solvents.

The amount of rinsing solvent which must be used is particularly large in the case of viscous and/or adhesive samples.

In addition, when different samples which are immiscible with one another are analyzed, it is necessary to use different types of rinsing solvent.

Added to that is the necessity periodically to carry out scaling operations in order to eliminate the solid deposits which have adhered strongly to the walls of the U-tube.

Those operations require the use of reagents based on very toxic strong acids, such as, by way of example, hot chromic acid solutions which are particularly aggressive and also carcinogenic.

SUMMARY OF THE INVENTION

The present invention provides a method for cleaning the U-tube of the measurement cell of a densimeter.

According to the invention, this method is characterized in that, after the analysis of a sample, a rinsing solvent is injected into the injection opening of the U-tube under pressure or by suction, and the stopper to which the base of the U-tube is secured is subjected to ultrasonic waves.

Those waves, which are propagated in the rinsing solvent, cause the U-tube to be set in vibration and, surprisingly, enable the action of the solvent to be intensified in such a manner as to eliminate the disadvantages of the conventional cleaning method.

When the cleaning method according to the invention is implemented, the ultrasonic radiation in fact acts on several levels.

In the first place, by being propagated, the ultrasonic waves increase convection within the solvent, in the volume of the U-tube, and simultaneously bring about its transformation into a foam capable of improving the transfer of mass between the solvent and the sample residues deposited on the walls of the U-tube.

Furthermore, the propagation of the ultrasonic waves in the solvent causes the implosion of cavitation bubbles in the vicinity of the inner walls of the U-tube.

This cavitation phenomenon increases the efficiency of cleaning the U-tube in as much as it permits, on the one hand, a reduction in the amount of solvent necessary to dissolve the sample residues deposited on the walls of the tube and, on the other hand, the elimination of residues of weakly viscous samples using a non-compatible solvent, that is to say, a solvent in which those residues are normally insoluble.

In addition, it was realised that, owing to the cavitation phenomenon, the use of ultrasonic waves also surprisingly permits the elimination of the solid deposits which have adhered strongly to the walls of the U-tube and therefore the removal of the necessity periodically to carry out scaling operations with toxic reagents.

The ultrasonic radiation also has the effect of nebulising the residues of weakly viscous samples which have been deposited on the walls of the U-tube.

This nebulisation phenomenon enables the drying time necessary after the injection of the second solvent to be significantly reduced, or even in some cases enables all of the residual drops of rinsing solvent to be atomised, even if that solvent is not volatile, thus rendering the injection of a drying solvent unnecessary.

According to another feature of the invention, a piezoelectric or magnetostrictive ultrasonic transducer is secured to the stopper of the measurement chamber.

The frequency of the vibrations induced by the ultrasonic radiation emitted and transmitted by that transducer is conditioned by the features thereof, the mass of the stopper on which the U-tube is mounted and the flexibility of the resilient seal.

That frequency is as a general rule from 20 to 200 kHz.

The power that has to be used depends to a large extent on the required cleaning action.

That power must be at a minimum in order to increase the transfer of mass between the rinsing solvent and the sample residues deposited on the walls of the U-tube as a result of the convection phenomenon but, on the other hand, it must be at a maximum in order to permit the initiation of the cavitation and nebulisation phenomena within the solvent.

In one form thereof, the present invention provides a method for cleaning the U-tube of the measurement cell of a densimeter, the measurement cell comprising:
- an isothermic enclosure which defines at its inner portion a measurement chamber (3) closed by a stopper (2) surrounded by a resilient seal (4);
- a U-tube (1) which is to be filled with a sample being analyzed and which extends inside the measurement chamber (3), the U-tube (1) being secured to the stopper at its base, which is formed by its free ends which project outwardly from the measurement chamber (3) in order to permit the injection of the sample being analyzed via an injection opening (6) and its evacuation via an evacuation opening (7); and
- means for causing the U-tube (1) to vibrate, characterized in that
after the analysis of a sample, a rinsing solvent is injected into the injection opening (6) of the U-tube (1) and the stopper (2) to which the base of the U-tube (1) is secured is subjected to ultrasonic waves.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

The sole Figure is a diagram representing a device permitting the implementation of this method.

Corresponding reference characters indicate corresponding parts. Although the exemplification set out herein illustrates an embodiment of the invention, the embodiment disclosed is not intended to be exhaustive or to be construed as limiting the scope of the invention to the precise form disclosed.

DETAILED DESCRIPTION

According to the FIGURE, the U-tube 1 extends inside an isothermic enclosure which defines at its inner portion a measurement chamber 3 shown diagrammatically by broken lines.

The measurement chamber 3 is closed by a stopper 2 surrounded by a resilient seal 4.

The U-tube 1 is secured to the stopper 2 at its base which is formed by its free ends.

As shown in the FIGURE, the free ends of the U-tube 1 project outwardly from the measurement chamber 3 in order to permit the injection of a sample being analyzed or solvents via an injection opening 6 and the removal thereof via an evacuation opening 7, as shown diagrammatically by the arrows.

An ultrasonic transducer 5 is secured to the stopper 2 to convert electrical energy into acoustic energy in the ultrasonic range.

Energy is transmitted to the stopper in order to cause the U-tube 1 to vibrate and to free it of the impurities which have been deposited on its walls.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A method for cleaning the U-tube of the measurement cell of a densimeter, the measurement cell comprising:
   an isothermic enclosure having a measurement chamber closed by a stopper surrounded by a resilient seal;
   a U-tube disposed within the measurement chamber for containing a sample being analysed, the U-tube secured to the stopper at a base of the U-tube which is formed by free ends which project outwardly from the measurement chamber to permit the injection of the sample via an injection opening and evacuation of the sample via an evacuation opening; and
   means for causing the U-tube to vibrate;
   said method comprising the steps of:
   analyzing a sample to determine the density of the sample;
   injecting a rinsing solvent into the injection opening of the U-tube; and
   subjecting the stopper to ultrasonic waves by actuation of a transducer different from the means for causing the U-tube to vibrate, the transducer secured to the stopper and operable to generate and transfer acoustic energy to the stopper to cause the U-tube to vibrate with propagation of the ultrasonic waves into the rinsing solvent.

2. The method of claim 1, wherein the transducer is selected from the group consisting of a piezoelectric ultrasonic transducer and a magnetostrictive ultrasonic transducer.

3. The method of claim 1, wherein said subjecting step comprises subjecting the stopper to ultrasonic waves at a frequency of from 20 to 200 kHz.

4. The method of claim 1, further comprising, following said subjecting step, the additional steps of:
   evacuating the rinsing solvent from the U-tube;
   injecting a drying solvent into the U-tube; and
   evacuating the drying solvent from the U-tube.

* * * * *